United States Patent [19]

Giuliani et al.

[11] 4,330,570
[45] May 18, 1982

[54] SELECTIVE PHOTOINDUCED CONDENSATION TECHNIQUE FOR PRODUCING SEMICONDUCTING COMPOUNDS

[75] Inventors: John F. Giuliani, Kensington, Md.; Abe Auerbach, Albany, N.Y.

[73] Assignee: The United States of America as represented by the Secretary of the Navy, Washington, D.C.

[21] Appl. No.: 257,028

[22] Filed: Apr. 24, 1981

[51] Int. Cl.³ .............................................. C23C 13/04
[52] U.S. Cl. ............................ 427/54.1; 204/157.1 R; 204/158 R; 427/64; 427/84
[58] Field of Search ...................... 427/53.1, 64, 54.1, 427/87; 204/157.1 L, 157.1 R, 158.1 L, 158.1 R

[56] References Cited

U.S. PATENT DOCUMENTS

| | | | |
|---|---|---|---|
| 3,547,635 | 12/1970 | Kennary et al. | 430/413 |
| 3,720,515 | 3/1973 | Stanley | 430/313 |
| 4,120,705 | 10/1978 | Shirland | 148/174 |
| 4,260,647 | 4/1981 | Dension et al. | 427/53.1 |

OTHER PUBLICATIONS

"Synthesis of Highly Conducting Films of Derivatives of Polyacetylene, (CH)x" Journal of the American Chemical Society, Feb. 1, 1978.

*Primary Examiner*—John H. Newsome
*Attorney, Agent, or Firm*—Robert F. Beers; William T. Ellis; Kenneth E. Walden

[57] ABSTRACT

A process for producing a variety of organic-inorganic luminescent and semiconductive compounds or materials in the form of a film deposited directly on the surface of a substrate by ultraviolet photoinduced condensation from gaseous reactants such as antimony pentafluoride $(SbF_5)_n$ and organic or inorganic halogen-containing compounds. The process provides a new class of antimony (Sb) doped luminescent and semiconductive materials which can be produced on any arbitrary size or shape substrate, or even on existing substrates of other semiconductive materials or chips, to form semiconductive devices. The process may be used in photoinducing luminescent panel displays or microelectronic circuits, such as integrated electrical or optical circuits.

16 Claims, 8 Drawing Figures

SELECTIVE PHOTOINDUCED CONDENSATION TECHNIQUE FOR PRODUCING SEMICONDUCTING COMPOUNDS

BACKGROUND OF THE INVENTION

It is known to deposit microelectronic circuits on a substrate by evaporating a photosensitive organic halogen-containing compound in the presence of radiation. It is also known that insulating organic films may be deposited on a solid substrate using interacting unsaturated organic monomers in the vapor state when excited by electron bombardment, gamma-rays, x-rays, gaseous discharges and by ultraviolet light radiation. All of the above tehniques except that of ultraviolet light requires sophisticated and expansive ancillary equipment. It is not known, however, to deposit organic or inorganic semiconductive films through a photolytic activation of the chemionization products of a variety of organic and inorganic halogen-containing compounds reacted with antimony pentafloruide $(SbF_5)n$.

SUMMARY OF THE INVENTION

The present invention relates to passing ultraviolet light through the gas phase chemionization reaction between antimony pentafluoride and a variety of organic and inorganic halogen-containing compounds onto a substrate surface where there is caused to condense an antimony-doped luminescent and semiconductive material in the form of a thin film. The gaseous compounds combine initially to form a loosely bound complex which, upon irradiation by ultraviolet light, stabilizes to a salt as a condensate on the substrate surface.

OBJECT OF THE INVENTION

It is therefore an object of this invention to provide a simple and inexpensive method of producing organic and inorganic luminescent and semiconductive compound materials in the form of thin films.

It is another object of this invention to provide a method of producing luminescent and semiconductive materials by passing ultraviolet light through a gaseous compound of antimony pentafluoride and selected halogen-containing compounds onto a substrate surface to photoinduce condensation of ion salts thereon in the form of a thin film.

It is still another object of this invention to provide a method of producing a luminescent and/or semiconductive film on a substrate of selected substrate material of any arbitrary material, size or shape.

It is another object of this invention to provide a method of forming a semiconductor device by condensing a film of semiconductive material on a preformed semiconductor substrate of another type.

Other objects of the invention will become apparent on the acquiring of an understanding of the invention described in the specification and encompassed in the claims.

BRIEF DESCRIPTION OF THE DRAWINGS

FIG. 4 illustrates a method wherein ultraviolet light is directed onto a substrate surface exposed to the reactive gases.

FIG. 5 illustrates a similar method wherein P-N junctions are formed in the presence of the reactant gases.

FIG. 6 illustrates another method similar to FIG. 5 for forming P-N-P junctions in the presence of the reactant gases.

FIG. 7 illustrates a method similar to that shown in FIG. 4 wherein a window forms the substrate.

FIG. 8 illustrates still another method of employing the invention wherein a screen of selected openings allow passage of photoinducing light onto the substrate surface.

DETAILED DESCRIPTION

Figure 2:
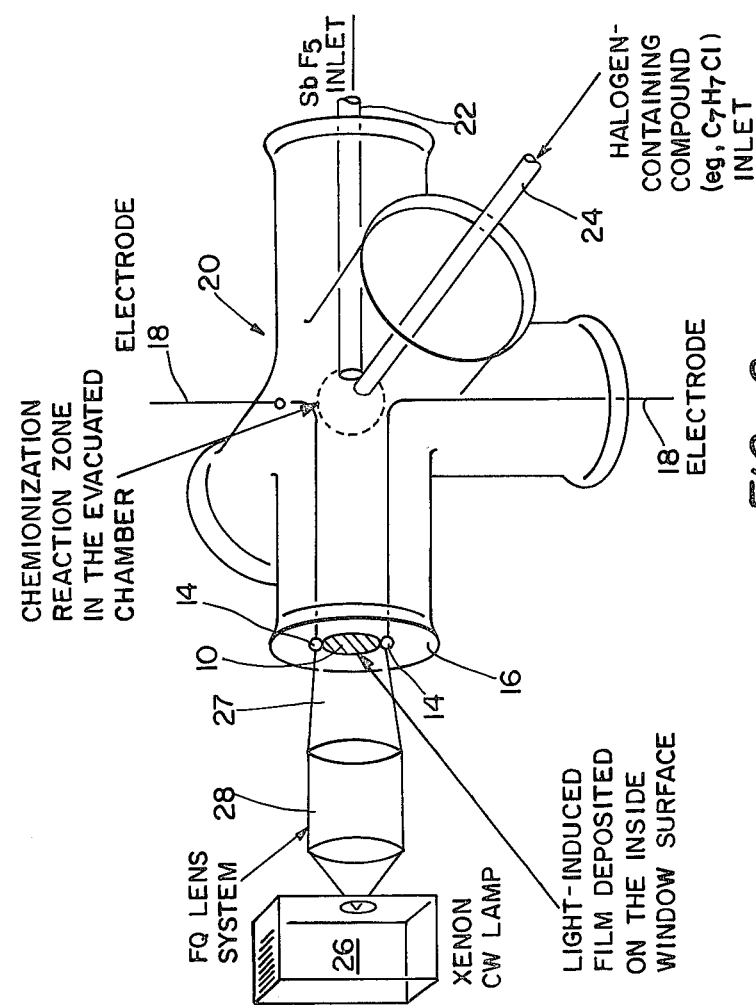
FIG. 2 shows apparatus for photocondensing ion salts from gaseous reactance.
Figure 1:
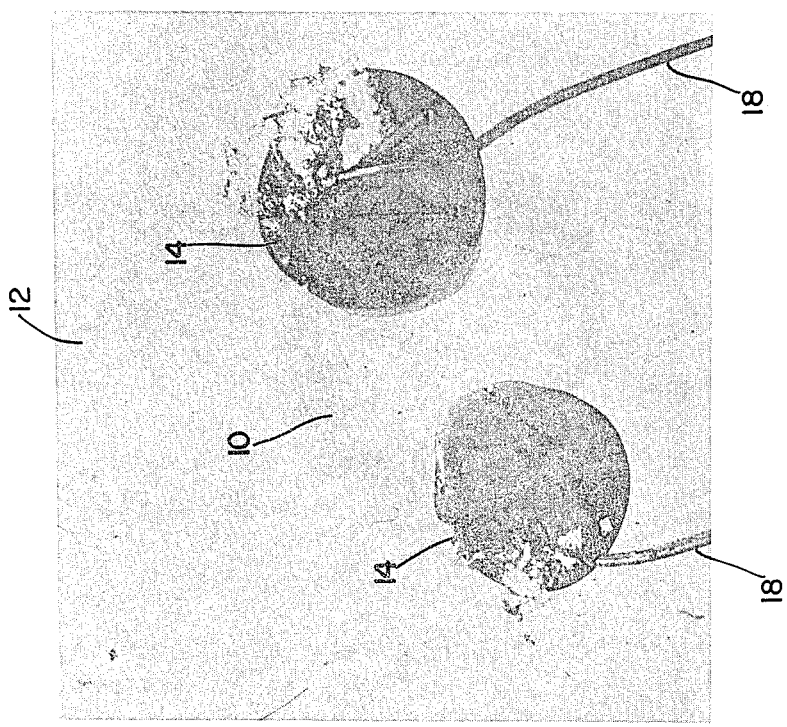
FIG. 1 is a photomicrograph of a luminescent or semiconductive material in the form of a thin film on a quartz window substrate to which silver contacts have been deposited.

Referring now to the drawings wherein like reference numerals designate, where possible, like or corresponding parts throughout the several figures, there is shown in FIG. 1 a photomicrograph 10X of film 10 deposited on a fused quartz (FQ) substrate 12 according to the process of the present invention. A pair of spaced-apart silver contacts 14 are deposited directly on a FQ substrate 12 to make electrical contact with film 10. A pair of leads 18 extend from spaced contacts 14. Window 16 previously, identified as substrate 12, is shown in FIG. 2 secured to one end of vessel or housing 20. This vessel is a vacuum chamber sealed except for two inlets 22 and 24 which are provided for admitting reactant gases. The entrances as shown in FIG. 2 are positioned 90° apart however, this is not a critical position and the gases may be admitted from other directions as well. The vessel is first evacuated by methods known in the art and thereafter the selected reactant gases, antimony pentafluoride $(SbF_5)$ and organic or inorganic halogen-containing compound, such as benzyl chloride $(C_7H_7Cl)$, are admitted to the reactive zone in the evacuated vessel 20 through inlets 22 and 24 respectively. Other halogens such as benzoyl chloride $(C_6H_5COCl)$, sulphur chloropentafluoride $(SF_5Cl)$, malonyl DIchloride $(CH_2CO_2Cl_2)$ and t-butlchloride $(CH_3)_3CCl)$ may be reacted with antimony pentafluoride for carrying out the process to be described. The gas compound diffuses from the reaction zone to completely fill the evacuated chamber of the vessel. The reaction pressure zone is monitored by a thermocouple gauge and capacitance manometer (not shown). The reactant gases are provided to enter the reaction zone in their gaseous states at room temperature. The benzyl chloride source is heated to around 350° C. to enhance its reactivity with $(SbF_5)n$. The reaction vessel is not heated. The total system is maintained at a pressure of about 10 μm, with about 5 μm contributed by each gas.

As shown in FIG. 2, a 150 watt unfiltered xenon CW Lamp 26 has its beam 27 focused by a 10-cm focused quartz lens system 28 through quartz window 16 on the inside of which may have been deposited spaced contacts 14 if resistivity measurement is desired. It is not necessary however, for the light output to be focused through a lens system in order to effect the inventive process. The process is independent of the focused light and there is no critical light source spacing or power density required to complete the process. The output of lamp 26 includes wavelengths of the ultravoilet (UV)

selected from around 2,000–4,000 Å which penetrates quartz window 16 into the presence of the reactant gases in contact therewith on the inside of vessel 20. The ultraviolet light in reaching the gases in contact with the inside window surface photoinduces condensation of a film 10 from the gas phase chemionization reaction between antimony pentafluoride (SbF$_5$) and a variety or organic or inorganic halogen-containing compounds such as previously identified.

When both reactants are simultaneously present, a film progressively condenses on the inside surface of the window (substrate) in the path of the ultraviolet light. This film has been found to be both luminescent and semiconductive, and its size conforms to the dimensions of the light beam itself.

EXAMPLE I

Figure 3:
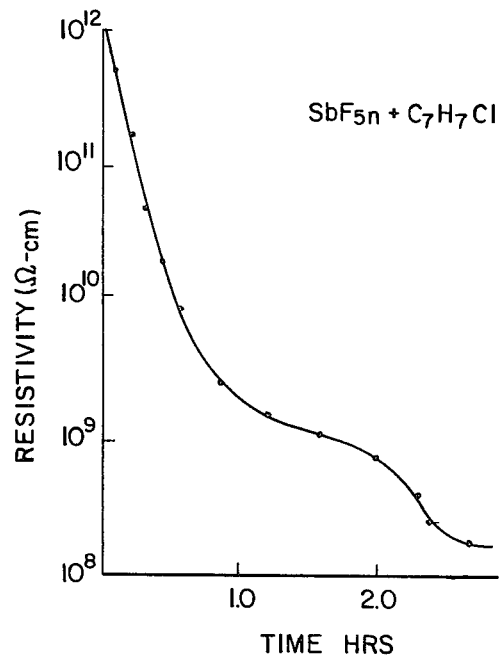
FIG. 3 is a graph illustrating electrical resistivity of the thin film versus its time of deposition on a substrate.

The chemionization between antimony pentafluoride and benzyl chloride in the presence of ultraviolet light as illustrated in FIG. 2 produced a film 1 $\mu$m thick on the substrate window in a period of about 2 hours. This film exhibited a decrease in electrical resistivity between contacts 14 of from $10^4$ to $10^5$ times the initial open circuit value of $10^{12}$ $\Omega$-cm. These resistive values as a function of deposit time are illustrated in FIG. 3. The gas phase chemionization reaction between antimony pentafluoride and benzyl chloride form the ion products (SbF$_5$)$_n$Cl$^-$ and C$_7$H$_7^+$. The reaction proceeds by way of a long lived intermediate state, probably a weakly bound ion pair. In our case we suspect that the gaseous antimony pentafluoride and benzyl chloride combine initially to form a loosely bound complex upon which irradiation stabilizes to a salt. This reaction is given by

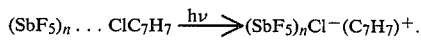

$$(SbF_5)_n \ldots ClC_7H_7 \xrightarrow{h\nu} (SbF_5)_nCl^-(C_7H_7)^+.$$

The blue luminescence of the deposited film probably arises from the presence of tropylium cations (C$_7$H$_7$)$^+$, and the electrical properties are also suggested from the above salt product. The precise structures of these photoinduced films are unknown. While the simultaneous appearance of luminescence and photoconductivity within the same material seens contradictory, this can be explained if the luminescence is associated with the capture of one type of charge carrier and the photoconductivity is connected with the other.

EXAMPLE II

In addition to the mixing of reactants benzyl chloride (C$_7$H$_7$Cl) and (SbF$_5$)$_n$ for the results reported under Example II to condense as a film 10 having resistivity characteristics reported in FIG. 3, other reactants with (SbF$_5$)n include malonyl chloride, succinyl chloride, benzoyl chloride, sulfur chloropentafluoride.

When benzyl chloride and (SbF$_5$)$_n$ are mixed, ion currents as high as $10^{-8}$ amps were measured. Similar currents were measured for the other halides when mixed with (SbF$_5$)$_n$ but their activation energies were generally higher, suggesting the formation of a condensed film when exposed to ultraviolet light which is less effective than that of benzyl chloride.

While the precise structure of the photocondensed film is presently unknown, its characteristics are known. There is directly fabricated by the disclosed process antimony doped semiconductive film which has a conductivity on the order of $10^{-8}(\Omega cm)^{-1}$ to $10^{-7}(\Omega cm)^{-1}$. This film is also photosensitive under visible light.

The discovery of this photocatalyzed effect would appear to have broad applicability to a wide variety of organic as well as inorganic halides which can be made to react with SbF$_5$ in the gas phase. Since these reactions generally proceed by a stable intermediate (i.e. ion pair), a large number of semiconductive films may be photocondensed by this technique.

Drawings (FIGS. 4–8) illustrate other arrangements of employing the method according to the disclosed invention. The essential feature in each embodiment is the condensation of the reactive gases as a salt on the substrate surface as a result of its exposure to ultraviolet light. In each case there is the novel gas phase chemionization reaction: (SbF$_5$)$_n$+RX→(SbF$_5$)$_n$X$^-$+R$^+$ (Where RX may be any one of a variety of organic or inorganic halogen containing compounds.

Figure 4:
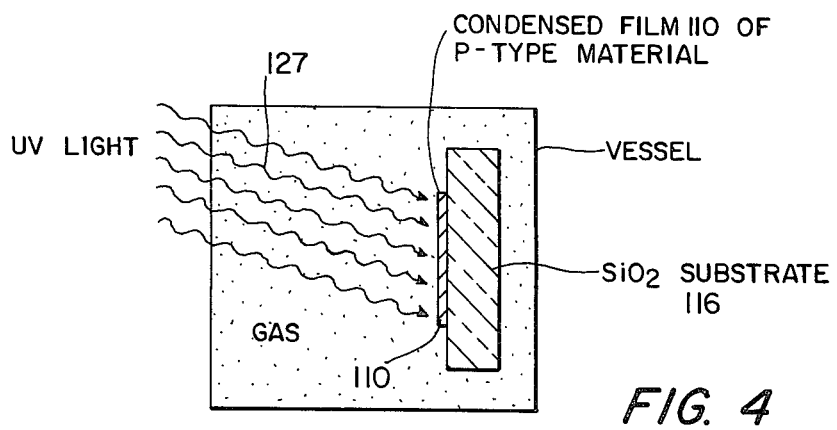
FIGS. 4–8 illustrate various arrangements for photoinduced condensation of a thin film of luminescent or semiconductive material on a substrate.

In FIG. 4 a gas mixture according to the above formula is contained within a vessel in which is located an SiO$_2$ substrate 116. The surface of the substrate is bathed in ultraviolet light 127 which causes condensation of a thin film 110 similar to film 10 in FIG. 2.

Figure 5:
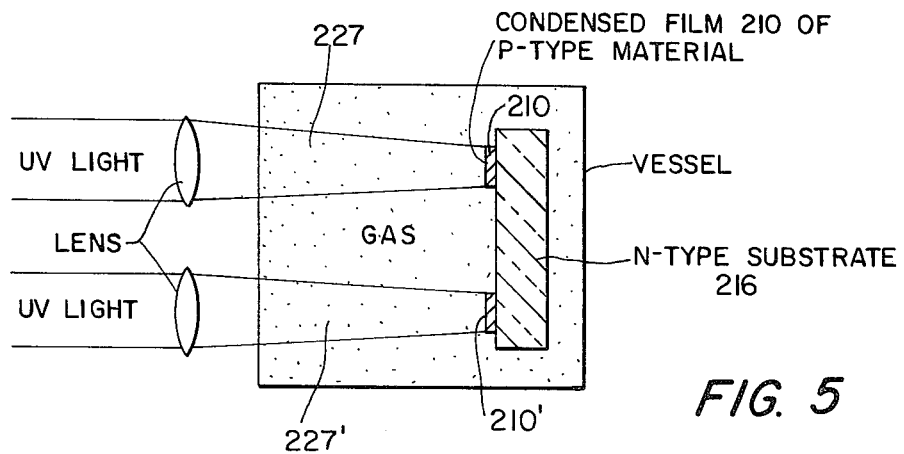

FIG. 5 illustrates another arrangement where ultraviolet lights 227 and 227' are focused to concentrate at two spaced-apart locations on the surface of substrate 216. Assuming the substrate to be N-type material, there may be deposited two-spaced apart film-like P-type 210 and 210' for establishing P-N junctions.

Figure 6:
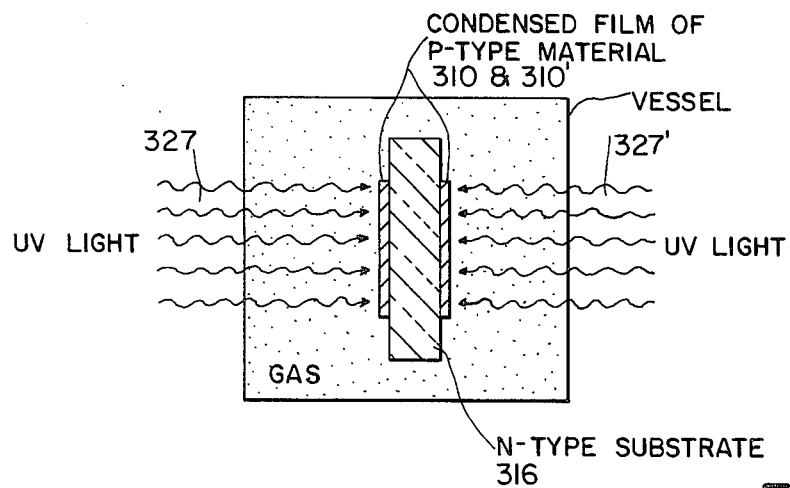
Figure 7:
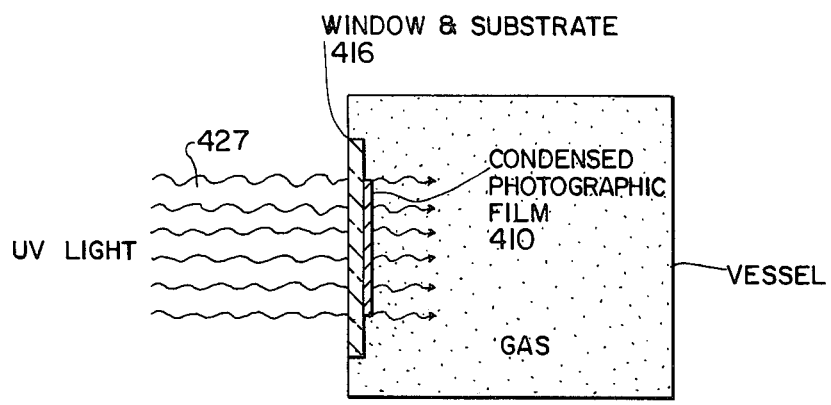

The process is carried one step further in FIG. 6 where ultraviolet light 327 and 327' is directed from different sources toward opposite faces of substrate 316 to form films 310 and 310' thereon. By this arrangement the substrate may be selected from a N-type material on which may be deposited on P-type film to form an P-N-P junction The process identified in FIG. 7 is very similar to that disclosed in FIG. 2. The gas reactants are contained within a vessel including a transparent window 416 defining the substrate and forming part of the vessel confining the gas. Ultraviolet light 427 passes through the window and reacts with the gases adjacent its inside surface where the gas is caused to condense thereon a salt defining film 410, i.e. an electro-photographic process to produce an image of a source (dry photography).

Figure 8:
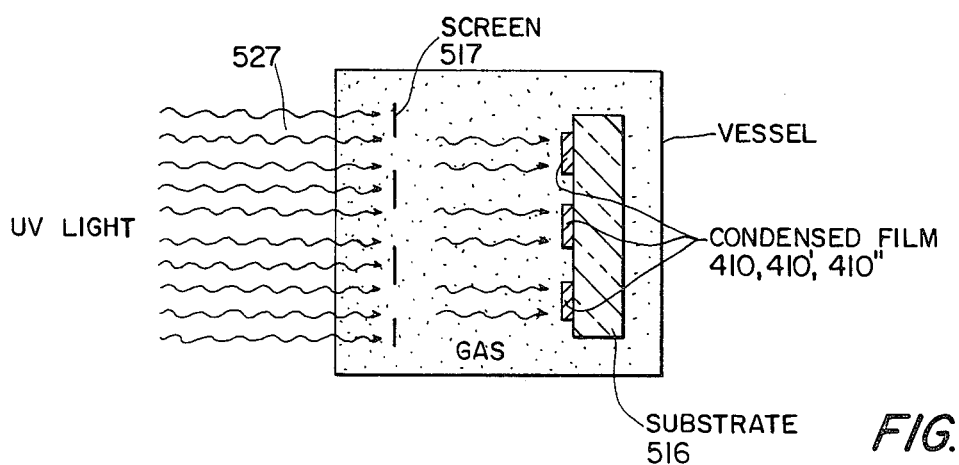

FIG. 8 illustrates a method of forming semiconductive films 410 and 410' and 410'' at spaced apart locations on substrate 516, by action of ultraviolet light 527 which passes through the openings of screen 517. The screen produces multiple light beams so that a number of semi-conductor devices or photographic images are produced simultaneously. An array of semiconductor devices may be formed when the substrate is of one type material and the condensed or deposited film is of another. The screen is used as a mask to selectively admit the ultraviolet light onto the substrate surface in a desired pattern. Since the process is capable of depositing a luminescent film on the substrate the screen may be used to provide a "nixi" display on the substrate.

The direct dependence of the film size on the dimension of the light beam gives rise to potential applications in maskless electro-photography as well as microelectronics. When a diffraction-limited light beam (i.e. a UV laser) is used selectively deposited film of micron dimensions is obtained.

There has been disclosed a method of producing antimony doped organic and inorganic luminescent and semiconductive materials in the form of a film condensate deposited on a substrate. When the film is deposited on a substrate of other type material, there may be provided a semiconductor device.

While the invention has been shown and described with reference to several embodiments it will be understood by those skilled in the art that various changes and modifications may be made thereto without departing from the spirit of the invention which is meant to be limited only by the scope of the claims annexed hereto.

What is claimed and desired to be secured by Letters Patent of the United States is:

1. A method of producing luminescent and semiconductive materials comprising:
   mixing reactive gases of antimony pentafluoride $(SbF_5)_n$ and a halogen containing compound in an evacuated chamber;
   providing a substrate having a surface in contact with the reactive gases; and
   passing ultraviolet light onto the substrate surface at its gas interface;
   whereby a film having luminescent and semiconductive characteristics is deposited on the substrate surface by photoinduced condensation from chemionization of the gases.

2. The method according to claim 1 further defined by selecting the halogen-containing compound from the group consisting of benzyl chloride ($C_7H_7Cl$), benzoyl chloride ($C_6H_5COCl$), surphur chloro-pentafluoride ($SF_5CL$), malonyl dichloride ($CH_2CO_2Cl_2$), succinyl chloride ($CH_2COCL$)$_2$ and t-butyl chloride ($CH_3)_3C Cl$).

3. The method according to claim 1 further defined by selecting benzyl chloride ($C_7H_7Cl$) as the halogen-containing compound.

4. The method according to claim 1 further defined by selecting benzoyl chloride ($C_6H_5COCl$) as the halogen-containing compound.

5. The method according to claim 1 further defined by selecting sulphur chloro-pentafluoride ($SF_5Cl$) as the halogen-containing compound.

6. The method according to claim 1 further defined by selecting malonyl dichloride ($CH_2CO_2Cl_2$) as the halogen-containing compound.

7. The method according to claim 1 further defined by selecting succinyl chloride ($CH_2COCL$)$_2$ as the halogen-containing compound.

8. The method according to claim 1 further defined by selecting t-butyl chloride [($CH_3)_3C Cl$)] as the halogen-containing compound.

9. The method according to claim 1 or 2 further defined by providing a substrate of one type semiconductive material to the surface of which is applied a semiconductive material of another type.

10. The method according to claim 3 further defined by providing a substrate of N-type material to at least one surface thereof is deposited a P-type material.

11. A method of producing semiconductive materials in the form of a thin film comprising:
    providing an evacuated chamber in which gas phase $(SbF_5)_n + RX$ react to form $(SbF_5)_nX^- + R^+$ wherein RX is a halogen-containing compound selected from the group consisting of benzyl chloride ($C_7H_7Cl$), benzoyl chloride ($C_6H_5COCl$), malonyl chloride ($CH_2CO_2Cl$) succinyl chloride ($CH_2COCl)_2$ and sulphur chloropentacluoride ($Sf_5Cl$);
    providing a substrate having at least one surface in contact with the reactant gases; and
    passing ultraviolet light onto the gas-contacting surface for condensing a semiconductive material on said surface.

12. The method according to claim 11 further defined by providing a substrate of semiconductive material.

13. The method according to claim 12 further defined by directing ultraviolet light onto separate areas of the gas-contacting surface.

14. A method of producing a luminescent semiconductive material in the form of a film comprising the steps of:
    providing an evacuated chamber in which antimony pentafluoride and benzyl chloride are reacted in gas phase to form ion products $(SbF_5)_nCl^-$ and $C_7H_7^+$;
    providing a substrate with at least one surface in contact with the gas reactants; and
    directing ultraviolet light onto said at least one gas-containing surface for stabilizing the gas to a salt which condenses as a film on said at least one surface.

15. A method according to claim 1, 11 or 14 further defined by providing a screen in the path of the ultraviolet light for selectively causing a film to be developed on the substrate surface for forming a luminescent display.

16. A method of forming a semiconductor device comprising the steps of:
    mixing gas phase antimony pentafluoride ($PbF_5)_n$ and benzyl chloride ($C_7H_7Cl$) reactants in an evacuated vessel;
    providing a chip of preselected semiconductive N-type material with at least one surface in contact with the gas reactants; and
    passing ultraviolet light onto said at lease one surface for photoinducing condensation thereon of a salt in the form of a film of P-type material.

* * * * *